United States Patent [19]

Ide et al.

[11] Patent Number: 4,760,054
[45] Date of Patent: Jul. 26, 1988

[54] MILBEMYCIN 5-CARBONATE DERIVATIVES AND COMPOSITIONS CONTAINING THEM

[75] Inventors: Junya Ide; Noritoshi Kitano, both of Hiromachi, Japan

[73] Assignee: Sankyo Company Limited, Tokyo, Japan

[21] Appl. No.: 780,391

[22] Filed: Sep. 26, 1985

Related U.S. Application Data

[63] Continuation of Ser. No. 670,337, Nov. 9, 1984, abandoned.

[30] Foreign Application Priority Data

Nov. 14, 1983 [JP] Japan ................... 58-213588

[51] Int. Cl.$^4$ ............... A61K 31/70; C07H 17/04; C07D 313/06
[52] U.S. Cl. ......................... 514/30; 536/7.1; 549/268; 71/88
[58] Field of Search ............ 549/268; 536/7.1; 514/30; 78/88; 71/88

[56] References Cited

U.S. PATENT DOCUMENTS

| | | | |
|---|---|---|---|
| 4,134,973 | 1/1979 | Fisher et al. | 536/7.1 |
| 4,156,720 | 5/1979 | Fisher et al. | 536/7.1 |
| 4,289,760 | 9/1981 | Mrozik et al. | 536/7.1 |
| 4,408,059 | 10/1983 | Smith, III et al. | 536/7.1 |
| 4,547,491 | 10/1985 | Mrojik et al. | 536/7.1 |

FOREIGN PATENT DOCUMENTS

| | | | |
|---|---|---|---|
| 0074758 | 3/1983 | European Pat. Off. | 549/264 |
| 0102721 | 3/1984 | European Pat. Off. | 546/7.1 |
| 0142969 | 5/1985 | European Pat. Off. | 536/7.1 |
| 0144285 | 6/1985 | European Pat. Off. | 514/30 |
| 2387231 | 12/1978 | France | 514/30 |
| 0139081 | 8/1982 | Japan | 549/264 |
| 0016894 | 1/1984 | Japan | 549/264 |
| 0020284 | 2/1984 | Japan | 549/264 |
| 0152490 | 8/1985 | Japan | 514/30 |
| 0184085 | 9/1985 | Japan | 549/268 |

*Primary Examiner*—J. R. Brown
*Assistant Examiner*—Elli Peselev
*Attorney, Agent, or Firm*—Frishauf, Holtz, Goodman & Woodward

[57] ABSTRACT

5-Carbonate derivatives of milbemycins $A_3$, $A_4$ and $A_5$ have valuable acaricidal, anthelmintic and other activities, especially against endo- and exoparasites.

29 Claims, No Drawings

MILBEMYCIN 5-CARBONATE DERIVATIVES AND COMPOSITIONS CONTAINING THEM

This is a continuatin of application Ser. No. 670,337 filed Nov. 9, 1984 now abandoned.

BACKGROUND OF THE INVENTION

The present invention relates to a series of new derivatives of the compounds known as "milbemycins", particularly of milbemycin $A_3$, milbemycin $A_4$ and milbemycin D.

Milbemycin D was disclosed in U.S. Pat. No. 4,346,171, where it was referred to as "compound B-41D", and milbemycins $A_3$ and $A_4$ were disclosed in U.S. Pat. No. 3,950,360. These compounds may be represented by the formula (I):

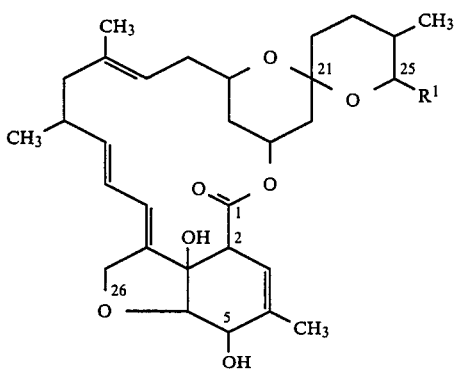

in which $R^1$ represents a methyl group, an ethyl group or an isopropyl group, these compounds being milbemycin $A_3$, milbemycin $A_4$ and milbemycin D, respectively. The numbering system shown on the above formula is that employed herein for all milbemycin derivatives, including the compounds of the present invention.

These milbemycin compounds may be isolated from cultures of the Streptomyces strain B-41-146, which has been deposited at the Fermentation Research Institute, Agency of Industrial Science and Technology, Ministry of International Trade and Industry, Japan, whence it is available under the accession number FERM-1438. The compounds have been found to have valuable anthelmintic and acaricidal activities.

Certain 5-(lower alkanoyl)oxy derivatives of milbemycin D are disclosed in Japanese patent application Kokai (i.e. laid open to public inspection) No. 120589/82. U.S. Pat. No. 4,201,861 discloses C-076 macrolide derivatives (similar to the milbemycins) in which there is an acyloxy group or a sugar-oxy group at the 5-position.

We have now discovered a series of derivatives of milbemycins $A_3$, $A_4$ and D which have demonstrated, in certain test systems, activities against specific endoparasites and ectoparasites better than the corresponding activities of their parent compounds.

BRIEF SUMMARY OF INVENTION

The compounds of the invention are 5-carbonate derivatives of milbemycins, and may be represented by the formula (II):

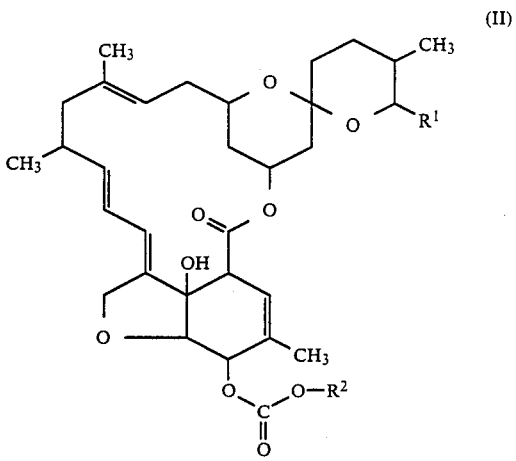

in which:

$R^1$ represents a methyl group, an ethyl group or an isopropyl group;

$R^2$ represents a group formed from an optionally protected sugar alcohol, sugar or aldonic acid by removal of the $\omega$-alcoholic hydroxy group therefrom, or a group of formula $-A-R^3$;

A represents an alkylene or alkylidene group;

$R^3$ represents a hydrogen or halogen atom, a group of formula $-Q-R^4$, a group of formula $-O.CO.R^5$ or a group of formula $-NH.CO.R^6$;

Q represents an oxygen or sulfur atom or an imino group;

$R^4$ represents a hydrogen atom, a $C_1-C_6$ alkyl group or a substituted $C_1-C_6$ alkyl group;

$R^5$ represents a $C_1-C_6$ alkyl group, a substituted $C_1-C_6$ alkyl group, an aryl group, a heterocyclic group or a group formed from an optionally protected aldonic or uronic acid by removal of one carboxy group;

$R^6$ represents a $C_1-C_6$ alkyl group or an aryl group; and the substituents on said substituted $C_1-C_6$ alkyl groups are at least one group selected from the group consisting of hydroxy, $C_1-C_6$ alkoxy, aryloxy, amino, acylamino, $C_1-C_6$ alkylamino, di($C_1-C_6$ alkyl)amino, arylamino, mercapto, $C_1-C_6$ alkylthio and arylthio groups.

The invention also provides an anthelmintic, acaricidal and insecticidal composition comprising an anthelmintic, acaricidal and insecticidal compound in admixture with a pharmaceutically, agriculturally or horticulturally acceptable carrier or diluent, wherein the compound is selected from the group consisting of compounds of formula (II).

The invention still further provides a method of treating an animal, which may be human or non-human, parasitized by a parasite selected from the group consisting of helminths, acarids and insects, which comprises applying to or administering to said animal an active compound, wherein said active compound is selected from the group consisting of compounds of formula (II).

The invention still further provides a method of protecting animals or plants from damage by parasites selected from the group consisting of acarids, helminths and insects, which comprises applying an active compound to said animals, to said plants or to seeds of said plants or to a locus including the same, wherein the active compound is selected from the group consisting of compounds of formula (II).

DETAILED DESCRIPTION OF INVENTION

Where $R^2$ represents a group derived from a sugar alcohol, this may be, for example, glycerol, erythritol, threitol, arabitol, adonitol, xylitol, sorbitol, mannitol or dulcitol.

Where $R^2$ represents a group derived from a sugar, this may be, for example, glyceraldehyde; an aldose such as erythrose, threose, arabinose, ribose, xylose, lyxose, glucose, mannose or galactose; a ketose such as fructose or sorbose; or a disccharide such as maltose, lactose or sucrose.

Where $R^2$ or $R^5$ represents a group derived from an aldonic acid, this may be, for example, arabonic acid, gluconic acid, mannonic acid or galactonic acid.

Where $R^5$ represents a group derived from a uronic acid, this may be, for example, glucuronic acid or galacturonic acid.

Examples of protecting groups for the hydroxy group of the above-mentioned sugar alcohols, sugars, aldonic acids and uronic acids are: an aliphatic acyl group, such as formyl or acetyl; a cyclic ether group such as tetrahydro-2-furanyl or tetrahydro-2-pyranyl; a 1-alkoxyethyl group such as 1-methoxyethyl or 1-ethoxyethyl; and a silyl group such as trimethylsilyl, triethylsilyl or t-butyldimethylsilyl. Other examples, when a single protecting group is to protect both hydroxy groups of the 1,2-diol or 1,3-diol moiety, are: alkylene, aralkylene or cycloalkylene groups, such as methylene, ethylene, isopropylene, benzylene or cyclohexylene. Examples of protecting groups for the carboxy group on aldonic acids and uronic acids are the t-butyl and 2,2,2-trichloroethyl groups.

The alkylene or alkylidene group represented by A is a $C_1$–$C_6$ alkylene or alkylidene group such as methylene, ethylene, ethylidene, trimethylene, propylene, propylidene, tetramethylene, pentamethylene or hexamethylene. We prefer the methylene and ethylene groups.

The halogen atom which may be represented by $R^3$ is a fluorine, chlorine, bromine or iodine atom and preferably chlorine or iodine.

In the compounds of formula (II), where $R^4$, $R^5$ or $R^6$ represents a $C_1$–$C_6$ alkyl group or a substituted alkyl group, this may be a straight or branched chain group and is preferably a $C_1$–$C_5$ alkyl group, for example a methyl, ethyl, propyl, butyl or pentyl group. It is preferably a $C_1$–$C_3$ alkyl group.

The alkyl moiety of the substituents, i.e. of the $C_1$–$C_6$ alkoxy group, the mono- or di($C_1$–$C_6$ alkyl)amino group or the $C_1$–$C_6$ alkylthio group, on the substituted alkyl group represented by $R^4$ and $R^5$ is preferably a methyl, ethyl or propyl group.

The aryl moiety of the substituents, i.e. of the aryloxy group, the arylamino group or the arylthio group, on the substituted alkyl group represented by $R^4$ and $R^5$ and the aryl group represented by $R^5$ and $R^6$ is preferably a phenyl, tolyl or naphthyl group, more preferably a phenyl group.

The acyl moiety of the acylamino substituent in the substituted alkyl group represented by $R^4$ and $R^5$ is preferably, an alkanoyl group (such as formyl, acetyl propionyl or butyryl) or a benzoyl group, more preferably an acetyl group.

Particularly preferred substituted alkyl groups represented by $R^4$ and $R^5$ include, for example, the 2-hydroxyethyl, 2-methoxyethyl, 2-ethoxyethyl, 2-phenoxyethyl, 2-aminoethyl, 2-formylaminoethyl, 2-acetylaminoethyl, 2-methylaminoethyl, 2-ethylaminoethyl, 2-dimethylaminoethyl, 2-mercaptoethyl, 2-methylthioethyl, 2-ethylthioethyl, 2-phenylthioethyl, 2-hydroxypropyl, 3-hydroxypropyl, 3-methoxypropyl, 3-ethoxypropyl, 3-aminopropyl, 3-dimethylaminopropyl, 3-mercaptopropyl, 3-methylthiopropyl, 2-hydroxybutyl, 4-hydroxybutyl, 4-aminobutyl, 4-dimethylaminobutyl, 4-mercaptobutyl, 2-hydroxypentyl and 5-hydroxypentyl groups.

Examples of heterocyclic groups which may be represented by $R^5$ include 5- or 6-membered cyclic groups containing a ring oxygen or a sulfur atom, particularly the furanyl, dihydrofuranyl, tetrahydrofuranyl, dihydropyranyl, tetrahydropyranyl, thienyl and tetrahydrothienyl groups, more preferably the pyranyl, dihydropyranyl and tetrahydropyranyl groups.

Some of the groups represented by $R^2$ in the compounds of formula (II) contain asymmetric carbon atoms and may thus form optically active compounds. These optically active compounds and also optically inactive forms, such as racemates, form part of the present invention. Particularly in the case of groups derived from sugar alcohols, sugars, aldonic acids, and uronic acids, both naturally occuring forms and forms which do not occur in nature may be employed.

Preferred classes of compound of formula (II) are as follows:

1. Compounds in which $R^2$ represents a group formed from an optionally protected sugar alcohol by removing the ω-alcoholic hydroxy group.
2. Compounds in which $R^2$ represents a group of formula —A—$R^3$ wherein:

A represents a $C_1$–$C_2$ alkylene group;

$R^3$ represents a halogen atom, a group of formula —Q—$R^4$ or a group of formula —OCOR$^5$;

Q represents an oxygen or sulfur atom;

$R^4$ represents a $C_1$–$C_3$ alkyl group or a substituted $C_1$–$C_3$ alkyl group, the substituent being selected from the hydroxy group, $C_1$–$C_3$ alkoxy groups, the amino group, acetylamino groups and mono- and di-($C_1$–$C_3$ alkyl)amino groups; and $R^5$ represents a $C_1$–$C_3$ alkyl group, a substituted $C_1$–$C_3$ alkyl group, the substituent being the same as defined for $R^4$ above, a 5- or 6-membered heterocyclic group containing the oxygen atom or a group formed from an optionally protected aldonic acid by removing the carboxy group.

3. Compounds in which $R^1$ represents an ethyl or isopropyl group (i.e. milbemycin $A_4$ and D derivatives).

Examples of compounds of the invention are listed below:

1. O$^5$-(chloromethoxycarbonyl)milbemycin D
2. O$^5$-(dichloromethoxycarbonyl)milbemycin D
3. O$^5$-(iodomethoxycarbonyl)milbemycin D
4. O$^5$-[(3,4-dihydro-2H-pyran-2-ylcarbonyloxy)methoxycarbonyl]milbemycin D
5. O$^5$-[(1,2,3,4-diisopropylidenegalacturonyloxy)methoxycarbonyl]milbemycin D
6. O$^5$-(N-acetylglycyloxymethoxycarbonyl)milbemycin D
7. O$^5$-(4-hyroxybutyryloxymethoxycarbonyl)milbemycin D
8. O$^5$-[2-(N,N-dimethylamino)ethylthiomethoxycarbonyl]milbemycin D
9. O$^5$-(2,2-dimethyl-1,3-dioxolan-4-ylmethoxycarbonyl)milbemycin D 10. O⁵-(2,3-dihydroxypropoxycarbonyl)milbemycin D
11. O⁵-(2,2-dimethyl-1,3-dioxolan-4-ylmethoxycarbonyl)milbemycin A₄
12. O⁵-(2,3-dihydroxypropoxycarbonyl)milbemycin A₄
13. O⁵-[(2-furylcarbonyloxy)methoxycarbonyl]milbemycin D
14. O⁵-[(3-furylcarbonyloxy)methyoxycarbonyl]milbemycin A₄
15. O⁵-[(4,5-dihydro-2-furylcarbonyloxy)methoxycarbonyl]milbemycin A₃
16. O⁵-[(4,5-dihydro-3-furylcarbonyloxy)methoxycarbonyl]milbemycin D
17. O⁵-[(tetrahydro-2-furylcarbonyloxy)methoxycarbonyl]milbemycin A₄
18. O⁵-[(tetrahydro-3-furylcarbonyloxy)methoxycarbonyl]milbemycin D
19. O⁵-[(tetrahydro-2-pyranylcarbonyloxy)methoxycarbonyl]milbemycin D
20. O⁵-[(2-thiophenecarbonyloxy)methoxycarbonyl]milbemycin A₄
21. O⁵-[(3-thiophenecarbonyloxy)methoxycarbonyl]milbemycin A₃
22. O⁵-[(tetrahydro-2-thiophenecarbonyloxy)methoxycarbonyl]milbemycin D
23. O⁵-[(tetrahydro-3-thiophenecarbonyloxy)methoxycarbonyl]milbemycin A₄
24. O⁵-[(2-pyridinecarbonyloxy)methoxycarbonyl]milbemycin D
25. O⁵-[(3-pyridinecarbonyloxy)methoxycarbonyl]milbemycin A₃
26. O⁵-[(4-pyridinecarbonyloxy)methoxycarbonyl]milbemycin A₄
27. O⁵-[(2-piperidinecarbonyloxy)methoxycarbonyl]milbemycin D
28. O⁵-[(3-piperidinecarbonyloxy)methoxycarbonyl]milbemycin D
29. O⁵-[(4-piperidinecarbonyloxy)methoxycarbonyl]milbemycin A₄
30. O⁵-[(2-pyrrolecarbonyloxy)methoxycarbonyl]milbemycin D
31. O⁵-[(3-pyrrolecarbonyloxy)methoxycarbonyl]milbemycin A₄
32. O⁵-[(2-pyrrolidinecarbonyloxy)methoxycarbonyl]milbemycin A₄
33. O⁵-[(3-pyrrolidinecarbonyloxy)methoxycarbonyl]milbemycin D
34. O⁵-(2-methyl-1,3-dioxolan-4-ylmethoxycarbonyl)milbemycin D
35. O⁵-(2,2-dimethoxy-1,3-dioxolan-4-ylmethoxycarbonyl)milbemycin D
36. O⁵-(2-phenyl-1,3-dioxolan-4-ylmethoxycarbonyl)milbemycin A₃
37. O⁵-(2,3,4-trihydroxybutoxycarbonyl)milbemycin A₄
38. O⁵-(2-hydroxy-3,4-isopropylidenedioxybutoxycarbonyl)milbemycin D
39. O⁵-(2,3-diacetoxypropoxycarbonyl)milbemycin D
40. O⁵-(2,3,4-triacetoxybutoxycarbonyl)milbemycin A₄
41. O⁵-(2,3,4,5-tetrahydroxypentoxycarbonyl)milbemycin D
42. O⁵-[2,3,4,5-bis(isopropylidenedioxy)pentoxycarbonyl]milbemycin A₄
43. O⁵-(1,2,3,4-di-O-isopropylidene-D-galactopyranyloxycarbonyl)milbemycin A₄
44. O⁵-(1,2,5,6-di-O-isopropylidene-D-glucoxycarbonyl)milbemycin D
45. O⁵-(D-galactopyranyloxycarbonyl)milbemycin D
46. O⁵-glucuronoylmilbemycin A₄

The components of the present invention may be prepared by either of the following Methods A and B.

Method A

Compounds of formula (II) may be prepared by reacting a compound of formula (I):

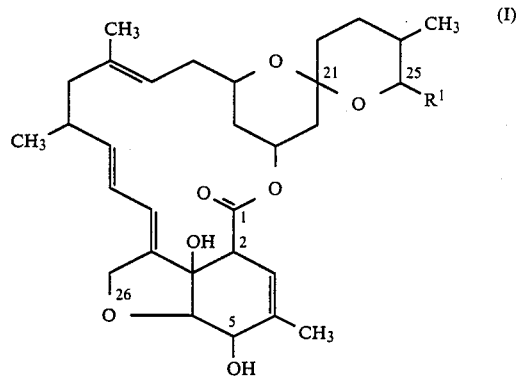

(in which R¹ is as defined above) with a halo compound of formula (III):

$$X.CO.OR^2 \qquad (III)$$

(in which X represents a halogen atom, preferably a chlorine or bromine atom, and R² is as defined above).

The reaction is preferably effected in the presence of an inert solvent and of a base. The base serves as an acid-binding agent and any base capable of serving this function without adversely affecting the reagents may be employed. The base is preferably an organic base, such as triethylamine, N, N-dimethylaniline, pyridine, 4-dimethylaminopyridine, 1,5-diazabicyclo[4.3.0]non-5-ene or 1,8-diazabicyclo[5.4.0]undec-7-ene. There is no particular limitation on the nature of the solvent to be employed in this reaction, provided that it has no adverse effect upon the reaction. Suitable solvents include: hydrocarbons, such as hexane, benzene, toluene or the xylenes; ethers, such as diethyl ether, tetrahydrofuran, dioxane or ethylene glycol dimethyl ether; esters, such as methyl acetate or ethyl acetate; or an excess of the organic base employed as acid-binding agent.

The reaction temperature is likewise not particularly critical and we normally prefer to carry out the reaction at a temperature within the range from 0° C. to 50° C. The time required for the reaction will, of course, vary depending upon the nature of the reagents, as well as the reaction temperature, but a period of from 30 minutes to 3 hours will normally suffice.

Where R² in the compound of formula (III) contains a hydroxy group, an amino group, a mercapto group or a carboxy group or two or more of these groups, the groups are preferably first protected, in order to inhibit side reactions. The protecting group is then, if necessary, removed after the reaction by conventional means. Suitable hydroxy-protecting groups include cyclic ether groups, 1-alkoxyethyl groups, silyl groups, alkylene groups, cycloalkylene groups and aliphatic acyl groups.

Where the hydroxy-protecting group is a cyclic ether group, a 1-alkoxyethyl group, a silyl group, an alkylene group or a cycloalkylene group, it is preferably removed by contacting the compound with an acid, in the presence of an inert solvent. The acid may be a mineral acid (such as hydrochloric acid, nitric acid or sulfuric acid) or an organic acid (such as acetic acid, trifluoroacetic acid, methanesulfonic acid, benzenesulfonic acid or p-toluenesulfonic acid). There is no particular limitation on the nature of the inert solvent to be employed, provided that it does not adversely affect the reaction. Suitable solvents include: hydrocarbons, such as hexane, benzene or toluene; ethers, such as diethyl ether, tetrahydrofuran or dioxane; alcohols, such as methanol, ethanol, propanol or ethylene glycol; water; and mixtures of any two or more of these solvents.

Where the hydroxy-protecting group is a silyl group, this is preferably removed by treating the compound with tetrabutylammonium fluoride at a temperature of from 0° C. to 100° C. for a period of from 30 minutes to 3 hours.

Where the hydroxy-protecting group is an aliphatic acyl group, it may be removed by treating the compound with a base, such as ammonia, in water or an alcohol (such as methanol or ethanol) at about room temperature for a period of from 30 minutes to 5 hours.

Preferred carboxy-protecting groups are the t-butyl and 2,2,2-trichloroethyl groups, and the preferred amino- and mercapto-protecting group is the t-butyl group. Where the protecting group is a t-butyl group, it may be removed by treatment with an acid, as described for removal of hydroxy-protecting groups above.

Where the carboxy-protecting group is a 2,2,2-trichloroethyl group, it may be removed by treating the compound with zinc and acetic acid at about room temperature for a period of from 30 minutes to 3 hours.

Method B

An alternative sequence of steps for preparing certain of the compounds of the invention is illustrated in the following reaction scheme:

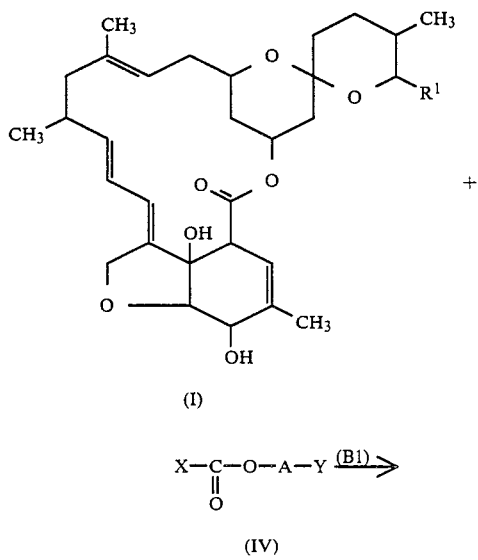

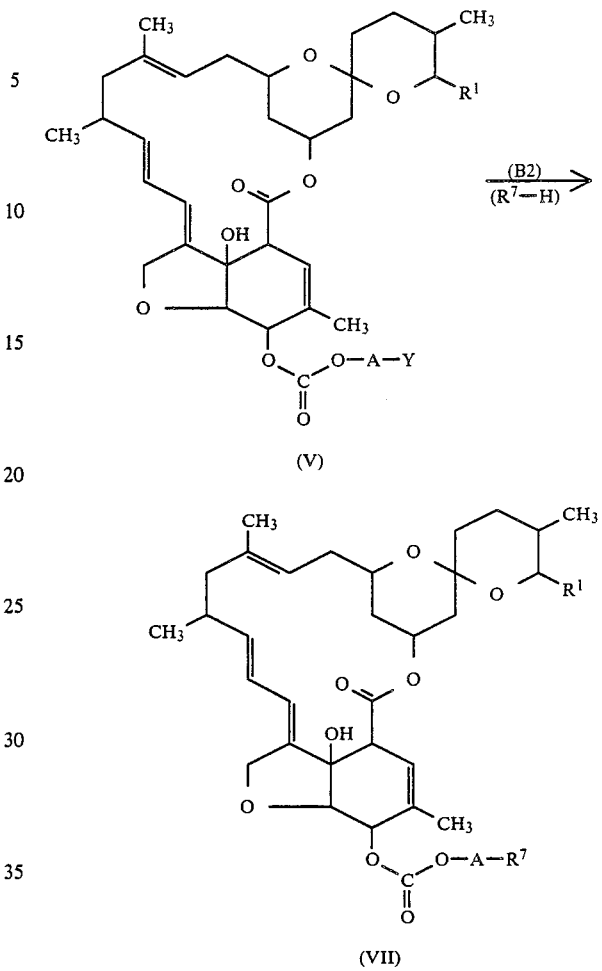

In the above formulae:

$R^1$, A and X are as defined above;

$R^7$ represents a group of formula $-Q-R^{4'}$ or a group of formula $-O.CO.R^5$ (in which Q and $R^5$ are as defined above and $R^{4'}$ represents a $C_1-C_6$ alkyl group or a substituted $C_1-C_6$ alkyl group, the substituents being as defined above); and Y represents a halogen atom, preferably a bromine or iodine atom.

Step (B1) in this process involves the preparation of a compound of formula (V) from the corresponding milbemycin of formula (I) by reaction with a compound of formula (IV). This step is analogous to the process of Method A and may be carried out under precisely the same conditions as described in relation to that process.

The resulting compound of formula (V) may, if necessary, be converted to an analogous compound having a different halogen atom Y in place of the original halogen atom. This reaction may be carried out by conventional means employed for halogen atom exchange.

For example, if the compound of formula (V) originally contains a chlorine or bromine atom as the atom represented by Y, and this is to be converted to a fluorine atom, the reaction is effected by reacting the starting material with potassium fluoride. Alternatively, if the compound of formula (V) originally contains a chlorine atom as the atom represented by Y, this may be converted to a bromine or iodine atom by reacting the starting material with an alkali metal bromide or iodide, respectively, particularly sodium bromide, potassium bromide, sodium iodide or potassium iodide.

These halogen exchange reactions are preferably effected in a polar solvent (such as acetonitrile or ethylene glycol) at a temperature of from 0° C. to 100° C. for a period of from 30 minutes to 5 hours. The halogen exchange reaction may be accelerated by the presence of a crown ether, for example 12-crown-4, 15-crown-5 or 18-crown-6.

In Step (B2), a compound of formula (VII) is prepared by reacting the compound of formula (V) with a compound of formula (VI):

$$R^7-H \qquad (VI)$$

(in which $R^7$ is as defined above) in an inert solvent.

Where $R^7$ represents a group of formula $-OR^{4'}$, $-SR^{4'}$ or $-O.CO.R^5$, we prefer that the compound of formula (VI) should be converted to its salt with an alkali metal (such as lithium, sodium or potassium) prior to or during the reaction. Where $R^7$ represents a group of formula $-O.CO.R^5$, the compound of formula (VI) may also be employed in the form of a salt with an organic amine, such as triethylamine or dicyclohexylamine.

Where $R^7$ represents a group of formula $-NH.R^{4'}$, the reaction of the compounds of formula (V) and (VI) is preferably effected in the presence of an organic amine (examples of which are given in Method A), although this is not essential.

The solvent employed for these reactions is not critical, provided that it has no adverse effect upon the reaction. Suitable solvents include:amides, such as dimethylformamide, dimethylacetamide or hexamethylphosphoric triamide; sulfoxides, such as dimethyl sulfoxide; ketones, such as acetone or methyl ethyl ketone; and nitriles, such as acetonitrile.

The reaction temperature is likewise not particularly critical, a preferred range of temperatures being from 0° C. to 100° C. The time required for the reaction will, of course, depend upon the nature of the reagents and on the reaction temperature, but a period of from 30 minutes to 5 hours will normally suffice.

If $R^7$ in the compound of formula (VI) employed in this reaction contains a hydroxy group, an amino group or a mercapto group, we prefer that such a group should be protected. After the reaction, the protecting group may, if necessary, be removed by conventional means. Protecting groups and methods of removing them are described above in Method A.

After completion of any of the above reactions, the desired product may be recovered from the reaction mixture by conventional means. For example, one suitable recovery technique comprises: pouring the reaction mixture (if necessary after removing the solvent by distillation) into iced water; if necessary, neutralising the mixture with a base or an acid; and then extracting the mixture with a water-immiscible organic solvent. After drying the organic extract and distilling off the solvent, the resulting residue can, if necessary, be further purified by such conventional techniques as recrystallisation and/or column chromatography.

The compounds of the invention have a strong acaricidal activity against, for example, adults, imagos and eggs of Tetranychus, Panonychus and rust mites, which are parasitic on fruit trees, vegetables and flowers. They are also active against Ixodidac, Dermanysside and Sarcoptidae, which are parasitic on animals. Further, they are active against: exoparasites, such as Oestrus, Lucilia, Hypoderma, Gasterophilus, lice and fleas, which are parasitic on animals and birds, particularly livestock and poultry; domestic insects, such as cockroaches and houseflies; and various other insects harmful to agriculture and horticulture, such as aphids and larval Lepidoptera. They are also effective against Meloidogyne in the soil, Bursaphelenchus and Phizoglyphus. They are also effective against insects of the orders Coleoptera, Homoptera, Heteroptera, Diptera, Thysanoptera, Orthoptera, Anoplura, Siphonaptera, Mallophage, Thysanura, Isoptera, Psocoptera, and Hymenoptera.

The compounds of the invention equally can be used to control other plant-damaging insects, particularly insects that damage plants by eating them. The compounds can be used to protect both ornamental plants and productive plants, particularly cotton (e.g. against *Spodoptera littoralis* and *Heliothis virescens*), as well as vegetable crops (e.g. against *Leptinotarsa decemlineata* and *Myzus persicae*) and rice crops (e.g. against *Chilo suppressalis* and *Laodelphax*).

The activity of the compounds of the invention is pronounced, both systemically and by contact. Accordingly, the compounds are very effective against sucking insects, especially sucking insects of the order Homoptera and most particularly the family Aphididae (such as *Aphis fabae, Aphis craccivora* and *Myzus persicae*), which are difficult to control with known compositions.

Accordingly, the compounds of the invention can be used to treat all manner of plants (as well as the seeds from which such plants are grown and the environment containing such plants) to protect them from insects such as those exemplified above. Such plants include cereals (e.g. maize or rice), vegetables (e.g. potatoes or soybeans), fruits and other plants (e.g. cotton).

The compounds of the invention can similarly be used to protect animals from a variety of ectoparasites, by applying the compounds to the animals or to the animals' environment, e.g. livestock housing, animal boxes, abattoirs, pasture land and other grasslands, as well as to any other places liable to be infested. The compounds may also be applied to external parts of the animals, preferably before they are infested.

Moreover, the compounds of the invention are effective against various parasitical helminths. These parasites can attack livestock, poultry and pet animals (such as pigs, sheep, goats, cows, horses, dogs, cats and fowl) and can cause grave economic damage. Among the helminths, the nematodes in particular often cause serious infection. Typical genera of nematodes which are parasitic on these animals and against which the compounds of the invention are effective include:

Haemonchus,
Trichostrongylus,
Ostertagia,
Nematodirus,
Cooperia,
Ascaris,
Bunostomum,
Oesophagostomum,
Chabertia,
Trichuris,
Strongylus,
Trichonema,
Dictyocaulus,
Capillaria, Heterakis,
Toxocara,
Ascaridia,
Oxyuris,
Ancylostoma,
Uncinaria,
Toxascaris and
Parascaris.

Certain parasitical species of the genera Nematodirus, Cooperia and Oesophagostomum attack the intestines, while certain species of the genera Haemonchus and Ostertagia parasitize the stomach, and parasites belonging to the genus Dictyocaulus are found in the lungs. Parasites belonging to the families Filariidae and Setariidae are found in internal tissues and organs, for example, the heart, the blood vessels, the subcutaneous tissues and the lymphatic vessels. The compounds of the invention are active against all these parasites.

The compounds of the invention are also effective against parasites which infect humans. Typical of the parasites which may most commonly be found in the digestive tracts of human beings are parasites of the genera Ancylostoma, Necator, Ascaris, Strongyloides, Trichinella, Capillaria, Trichuris and Enterobius. The compounds are also active against parasites of the genera Wuechereria, Brugia, Onchocerca and Loa of the family Filariidae (which are found in blood, tissues and other organs in addition to the digestive tract and are of medical importance), parasites of the genus Dracunculus and parasites of the genera Strongyloides and Trichinella, which especially infect the exointestinal canal.

The form of the compositions of the invention and the nature of the carriers or diluents employed in them will vary depending upon the intended use of the composition. For example, where the compounds of the invention are to be employed as anthelmintics for humans and other animals, they are preferably administered orally, parenterally or topically and the form of compositions chosen will be appropriate to the intended route of administration.

For oral administration, the composition of the invention is preferably in the form of a liquid drink comprising a non-toxic solution, suspension or dispersion of the active compound in water or another non-toxic liquid, in admixture with a suspending agent (such as bentonite), a wetting agent or other diluents. The drink, in general, also contains an anti-foaming agent. The active compound would normally be present in the drink in an amount of from 0.01 to 0.5% by weight, more preferably from 0.01 to 0.1% by weight.

Compositions for oral administration may also be in the form of dry solids, preferably in unit dosage form, such as capsules, pills or tablets containing the desired amount of the active compound. These compositions may be prepared by mixing the active compound uniformly with suitable finely ground diluents, fillers, disintegrators and/or binding agents, for example starch, lactose, talc, magnesium stearate and vegetable gum. The weight and contents of the preparation will vary widely, depending upon the nature of the animal to be treated, the degree of infection, the nature of the parasite and the body weight of the animal to be treated.

The compounds may also be administered as an additive to animal feedstuffs, in which case they may be dispersed uniformly in the feedstuffs, used as a top dressing or used in the form of pellets. The content of active compound in the feedstuff is preferably from 0.0001 to 0.02%, in order to achieve the desired anthelmintic activity.

For parenteral administration, the compound of the invention is preferably dissolved or suspended in a liquid vehicle, preferably a vegetable oil, such as peanut oil or cottonseed oil. Depending upon the animal to be treated, the injection may be subcutaneous or into the proventriculus, a muscle or the trachea. Such preparations would normally contain the active compound at a concentration of from 0.05 to 50% by weight.

The compounds of the invention may also be administered topically in admixture with a suitable carrier, such as dimethyl sulfoxide or a hydrocarbon solvent. Such preparations would be applied directly to the outside of the animal by spraying (e.g. by a hand spray or in spray races), by dipping (e.g. in a plunge dip), by a pour-on solution or by manual methods (e.g. hand-dressing).

The dose of active compound may be varied, depending upon the nature of the animal to be treated, and the nature and degree of parasitic infection. However, best results for oral administration are achieved when the dose is from 0.01 to 100 mg, more preferably from 0.5 to 50 mg, per 1 kg body weight. The compound may be administered in a single dose or in divided doses for a relatively short period, such as from 1 to 5 days.

Where the composition of the invention is intended for agricultural or horticultural use, a variety of forms and formulations are possible. For example, it may be formulated as dusts, coarse dusts, soluble powders, microgranules, fine microgranules, wettable powders, dilute emulsions, emulsifiable concentrates, aqueous or oily suspensions or solutions (which may be directly sprayable or for dilution), aerosols or capsules in, for example, polymeric substances. The carrier employed may be natural or synthetic and organic or inorganic; it is generally employed to assist the active compound to reach the part to be treated, and to make it easier to store, transport or handle the active compound. Solid, liquid and gaseous carriers may be employed, chosen from carriers well known in the art for use with compositions of this type.

Such formulations may be prepared by conventional means, e.g. by intimate mixing and/or ginding of the active ingredient(s) with the carrier or diluent, e.g. solvent, solid carrier or, optionally, surface-active agent.

Suitable solvents include: aromatic hydrocarbons, preferably the $C_8$ to $C_{12}$ fractions from petroleum distillation, such as xylene mixtures or substituted naphthalenes; esters of phthalic acid, such as dibutyl or dioctyl phthalate; aliphatic or alicyclic hydrocarbons, such as cyclohexane or the paraffins; alcohols and glycols or ethers derived from them, such as ethanol, ethylene glycol, ethylene glycol monomethyl ether or ethylene glycol monoethyl ether; ketones, such as cyclohexanone; strongly polar solvents, such as N-methyl-2-pyrrolidone, dimethyl sulphoxide or N,N-dimethylformamide; optionally epoxidized vegetable oils, such as epoxidized coconut oil or soybean oil; and water.

Solid carriers, which may be used, for example, in dusts and dispersible powders, include natural mineral fillers, such as calcite, talc, kaolin, montmorillonite or attapulgite. In order to improve the physical properties of the composition, it is also possible to add highly dispersed silicic acid or highly dispersed absorbent polymers. Suitable granulated adsorptive carriers may be porous (such as pumice, ground brick, sepiolite or bentonite) or non-porous (such as calcite or sand). A wide variety of pregranulated materials, organic or inorganic, may also be used; examples include dolomite and ground plant residues.

Surface-active agents which may be used are well known in the art and may be non-ionic, cationic or anionic agents having good emulsifying, dispersing and wetting properties. Mixtures of such agents may also be used.

The compositions may also contain stabilizers, antifoaming agents, viscosity regulators, binders or adhesives or any combination thereof, as well as fertilizers or other active substances to achieve special effects.

Pesticidal compositions will generally contain: from 0.01 to 99%, more preferably from 0.1 to 95%, by weight of the active compound; from 1 to 99.99% of a solid or liquid additive; and from 0 to 25%, more preferably from 0.1 to 25%, of a surface-active agent. Whereas commercial products are generally sold as concentrated compositions, they are generally diluted by the end-user to a concentration of active ingredient of from 0.001 to 0.0001% by weight (from 10 to 1 ppm).

The invention is further illustrated by the following Examples, of which Examples 1 to 11 illustrate the preparation of various compounds of the invention, Examples 12 to 14 demonstrate the activity of compounds of the invention and the preparation of a starting material for certain of the Examples is illustrated in the Preparation.

PREPARATION 2,2-Dimethyl-1,3-dioxolan-4-ylmethyl chloroformate 10 ml of a 10% w/v solution of phosgene in benzene were added to a solution of 1.0 g of 2,3-isopropylideneglycerol in 5 ml of methylene chloride, and the mixture was allowed to react overnight at room temperature. The mixture was then concentrated by evaporation under reduced pressure, giving 1.47 g of the title compound as a liquid.

Infrared Absorption Spectrum (liquid film) $\nu_{max}$ cm$^{-1}$:1775.

EXAMPLE 1

(a) $O^5$-(Chloromethoxycarbonyl)milbemycin D (b) $O^5$-(dichloromethoxycarbonyl)milbemycin D A solution of 158 mg of pyridine in 5 ml of benzene was added dropwise, whilst ice-cooling, to a solution of 1.11 g of milbemycin D and 243 mg of impure chloromethoxycarbonyl chloride (containing 40% by weight of dichloromethoxycarbonyl chloride) in 10 ml of benzene. The mixture was then allowed to react at room temperature for 1 hour, after which a further 30 mg of the impure chloromethoxycarbonyl chloride and 20 mg of pyridine were added. The mixture was stirred at room temperature for 30 minutes, and then ethyl acetate was added. The mixture was washed, in turn, with water, with dilute hydrochloric acid, with water, with an aqueous solution of sodium bicarbonate and again with water, after which it was dried over anhydrous sodium sulfate. The solvent was then removed by evaporation under reduced pressure. The residue was purified by column chromatography through silica gel using, as eluents, mixtures of hexane and ethyl acetate ranging from pure hexane to a volume ratio of 7:3. There were obtained 627 mg of the title monochloromethoxy compound, as well as 380 mg of the corresponding dichloromethoxy compound.

Chloromethoxy Compound

Infrared Absorption Spectrum (Nujol-trademark-mull)
$\nu_{max}$ cm$^{-1}$:3475, 1770, 1740, 1710.

Nuclear Magnetic Resonance Spectrum (CDCl$_3$) $\delta$ ppm:
1.53 (3H, singlet, 14—CH$_3$);
1.82 (3H, broad singlet, 4—CH$_3$);
4.65 (2H, broad singlet, 26—CH$_2$);
5.70 (1H, doublet, J=6.0Hz, —CHHCl);
5.81 (1H, doublet, J=6.0Hz, —CHHCl).
Mass Spectrum (m/e): 648 (M+), 209, 181.

Dichloromethoxy compound

Infrared Absorption Spectrum (Nujol mull)
$\nu_{max}$ cm$^{-1}$:3470, 1780, 1705.

Nuclear Magnetic Resonance Spectrum (CDCl$_3$) $\delta$ ppm:
1.53 (3H, singlet, 14—CH$_3$);
1.84 (3H, broad singlet, 4—CH$_3$);
5.66 (2H, broad singlet, 26—CH$_2$);
7.72 (1H, singlet, —CHCl$_2$).
Mass Spectrum (m/e): 682 (M+), 209, 181.

EXAMPLE 2

$O^5$-(Iodomethoxycarbonyl)milbemycin D

A suspension of 1.18 g of $O^5$-(chloromethoxycarbonyl)milbemycin D (prepared as described in Example 1) and 0.85 g of sodium iodide in 10 ml of acetonitrile was heated under reflux for 1 hour and then diluted with ethyl acetate. The diluted mixture was washed, in turn, with an aqueous solution of sodium thiosulfate and with water, after which it was dried over anhydrous sodium sulfate and evaporated to dryness under reduced pressure. The residue was purified by column chromatography through silica gel eluted with a 8:2 by volume mixture of hexane and ethyl acetate, giving 950 mg of the title compound.

Nuclear Magnetic Resonance Spectrum (CDCl$_3$) $\delta$ ppm:
1.52 (3H, singlet, 14—CH$_3$);
1.80 (3H, broad singlet, 4—CH$_3$);
4.59 (2H, broad singlet, 26—CH$_2$);
5.90 (2H, singlet, —CH$_2$I).

EXAMPLE 3

$O^5$-(3,4-Dihydro-2H-pyran-2-ylcarbonyloxy)methoxycarbonylmilbemycin D

A solution of 200 mg of $O^5$-(iodomethoxycarbonyl)milbemycin D (prepared as described in Example 2) and 52.7 mg of sodium 3,4-dihydro-2H-pyran-2-ylcarboxylate in 2 ml of dimethylacetamide was stirred at room temperature for 1 hour. The reaction mixture was then diluted with ethyl acetate, washed with water, dried over anhydrous sodium sulfate and finally evaporated to dryness under reduced pressure. The residue was purified by column chromatography through silica gel, eluted with a 8:2 by volume mixture of hexane and ethyl acetate, giving 175 mg of the title compound.

Infrared Absorption Spectrum (Nujol mull)
$\nu_{max}$ cm$^{-1}$:3475, 1765, 1740, 1710, 1650.

Nuclear Magnetic Resonance Spectrum (CDCl$_3$) $\delta$ ppm:
1.53 (3H, singlet, 14—CH$_3$);
1.82 (3H, broad singlet, 4—CH$_3$);
4.65 (2H, broad singlet, 26—CH$_2$);

5.80 (1H, doublet, J=8.0Hz, —OCHHO-);
5.93 (1H, doublet, J=8.0Hz, —OCHHO-);
6.43 (1H, doublet, J=6.0Hz, 6—H of pyran).
Mass Spectrum (m/e) 740 (M+), 209, 181.

EXAMPLE 4

$O^5$-(1,2,3,4-Di-O-isopropylidenegalacturonyloxy)methoxycarbonylmilbemycin D

A suspension of 1.7 g of $O^5$-(chloromethoxycarbonyl)milbemycin D (prepared as described in Example 1) and 1.2 g of sodium iodide in 30 ml of acetonitrile was heated under reflux for 1.5 hours and then evaporated to dryness under reduced pressure. Ethyl acetate was added to the residue, and then the mixture was washed with water, dried over anhydrous sodium sulfate and then evaporated to dryness under reduced pressure, to give 2.047 g of the crude iodo compound.

The whole of this crude iodo compound was dissolved in 10 ml of dimethylacetamide. 960 mg of potassium 1,2,3,4-diisopropylidenegalacturonate were added to the solution and the mixture was stirred at room temperature for 1 hour. It was then diluted with ethyl acetate, washed with water, dried over anhydrous sodium sulfate and then evaporated to dryness under reduced pressure. The residue was subjected to column chromatography through silica gel eluted successively with mixtures of hexane and ethyl acetate ranging in proportions from 9:1 to 6:4. The product was then further purified on a silica gel Lobar (trade mark) column (manufactured by Merck and Co. Inc., size B) eluted with a 1:9 by volume mixture of ethyl acetate and chloroform, to give 1.5 g of the title compound.

Infrared Absorption Spectrum (Nujol mull)
$\nu_{max}$ cm$^{-1}$:3500, 1790, 1765, 1710.
Nuclear Magnetic Resonance Spectrum (CDCl$_3$) δ ppm;
  1.33 (6H, singlet, 2×CH$_3$ of isopropylidene);
  1.44 (3H, singlet, 14—CH$_3$);
  1.53 (6H, singlet, 2×CH$_3$ of isopropylidene);
  1.82 (3H, broad singlet, 4—CH$_3$);
  4.63 (2H, broad singlet, 26—CH$_2$).
Mass Spectrum (m/e): 886 (M+), 209, 181.

EXAMPLE 5

$O^5$-(N-Acetylglycyloxymethoxycarbonyl)milbemycin D 131 mg of triethylamine were added to a solution of 740 mg of $O^5$-(iodomethoxycarbonyl)milbemycin D (prepared as described in Example 2) and 152 mg of N-acetylglycine in 10 ml of dimethylacetamide, and the mixture was stirred at room temperature for 30 minutes. It was then diluted with ethyl acetate, washed with water, dried over anhydrous sodium sulfate, and then evaporated to dryness under reduced pressure. The residue was purified by column chromatography through silica gel, eluted with mixtures of hexane and ethyl acetate ranging in proportions from 1:1 to 1:9, to give 470 mg of the title compound.

Infrared Absorption Spectrum (Nujol mull) δ$_{max}$ cm$^{-1}$:3350, 1765, 1740, 1660.
Nuclear Magnetic Resonance Spectrum (CDCl$_3$) δ ppm:
  1.54 (3H, singlet, 14—CH$_3$);
  1.83 (3H, broad singlet, 4—CH$_3$);
  2.04 (3H, singlet, acetyl);
  4.65 (2H, broad singlet, 26—CH$_2$);
  5.86 (2H, singlet, —OCH$_2$O—);
  6.17 (1H, broad singlet, NH).
Mass Spectrum (m/e): 556 (M+-173), 209, 181.

EXAMPLE 6

$O^5$-(4-Hydroxybutyryloxymethoxycarbonyl)milbemycin D 500 mg of $O^5$-(iodomethoxycarbonyl)milbemycin D (prepared as described in Example 2) were added, whilst ice-cooling, to a suspension of 176 mg of sodium 4-hydroxybutyrate in 5 ml of dimethylacetamide, and the mixture was stirred at room temperature for 30 minutes. It was then diluted with a 2:1 by volume mixture of ethyl acetate and hexane, washed with water, dried over anhydrous sodium sulfate and evaporated to dryness under reduced pressure, giving 430 mg of the title compound.

Infrared Absorption Spectrum (Nujol mull)
$\nu_{max}$ cm$^{-1}$:3475, 1765, 1740, 1710.
Nuclear Magnetic Resonance Spectrum (CDCl$_3$) δ ppm:
  1.53 (3H, singlet, 14—CH$_3$);
  1.82 (3H, broad singlet, 4—CH$_3$);
  2.52 (2H, triplet, J=7.0Hz, —OCOCH$_2$—);
  3.69 (2H, triplet, J=6.0Hz, —CH$_2$OH);
  4.66 (2H, broad singlet, 26—CH$_2$);
  5.83 (2H, singlet, —OCH$_2$O—).
Mass Spectrum (m/e): 556 (M+-160), 209, 181.

EXAMPLE 7

$O^5$-[2-(N,N-Dimethylamino)ethylthiomethoxycarbonyl]milbemycin D

A sodium methoxide solution was prepared from 10 ml of methanol and 200 mg of a 55% w/w suspension of sodium hydride in mineral oil. 326 mg of N,N-dimethylaminoethanethiol hydrochloride, followed by 1.7 g of $O^5$-(iodomethoxycarbonyl)milbemycin D (prepared as described in Example 2), were added, whilst cooling the solution with ice. The mixture was stirred at room temperature for 30 minutes and then diluted with ethyl acetate. It was then washed with water and then with an aqueous solution of sodium thiosulfate, after which it was dried over anhydrous sodium sulfate and evaporated to dryness under reduced pressure. The residue was purified by column chromatography through silica gel eluted with chloroform and methanol in proportions ranging from pure chloroform to a 95:5 by volume mixture. It was then further purified by chromatography through a silica gel Lobar column (Merck, size B), eluted with a 90:7:3 by volume mixture of chloroform, isopropanol and methanol, to give 530 mg of the title compound.

Infrared Absorption Spectrum (Nujol mull)
$\nu_{max}$ cm$^{-1}$:3475, 1745, 1710.
Nuclear Magnetic Resonance Spectrum (CDCl$_3$) δ ppm:
  1.53 (3H, singlet, 14—CH$_3$);
  1.83 (3H, broad singlet, 4—CH$_3$);
  2.27 (6H, singlet, 2×CH$_3$ of dimethylamino);
  2.45-2.95 (4H, multiplet, —SCH$_2$CH$_2$—N);
  4.65 (2H, broad singlet, 26—CH$_2$);
  5.30 (2H, singlet, —OCH$_2$S—).
Mass Spectrum (m/e): 556 (M+-161), 209, 181.

EXAMPLE 8

$O^5$-(2,2-Dimethyl-1,3-dioxolan-4-ylmethoxycarbonyl)-milbemycin D 1.47 g of 2,2-dimethyl-1,3-dioxolan-4-ylmethyl chloroformate (prepared as described in the Preparation) was added dropwise, in two portions, to an ice-cooled solution of 0.60 g of milbemycin D and 1 ml of pyridine in 10 ml of ethyl acetate. The mixture was allowed to react at the same temperature for 1 hour, at the end of which time ethyl acetate was added. The mixture was then washed, in turn, with water, an aqueous solution of potassium bisulfate, an aqueous solution of sodium bicarbonate and an aqueous solution of sodium chloride, and then dried over anhydrous sodium sulfate. The solvent was removed by distillation under reduced pressure, and the residue was purified by column chromatography through silica gel, eluted with chloroform and ethyl acetate in proportions ranging from 100% chloroform to a 20:1 by volume mixture. 0.80 g of the title compound was obtained in the form of a glass.

Infrared Absorption Spectrum (Nujol mull)
$v_{max}$ cm$^{-1}$:3410, 1725.

Nuclear Magnetic Resonance Spectrum (CDCl$_3$) δ ppm:
1.33 (3H, singlet, CH$_3$ at 2- position of dioxolane);
1.40 (3H, singlet, CH$_3$ at 2- position of dioxolane);
1.51 (3H, singlet, 14—CH$_3$);
1.78 (3H, broad singlet, 4—CH$_3$);
4.01 (1H, singlet, 7—OH);
4.56 (2H, broad singlet, 26—CH$_2$).

Mass Spectrum (m/e): 714 (M$^+$), 537, 519.

EXAMPLE 9

$O^5$-(2,3-Dihydroxypropoxycarbonyl)milbemycin D

A solution of 0.70 g of $O^5$-(2,2-dimethyl-1,3-dioxolan-4-ylmethoxycarbonyl)milbemycin D (prepared as described in Example 8), 7 ml of acetic acid and 21 ml of water was allowed to react at 40° C. for 3 hours. At the end of this time, the solvent was distilled off under reduced pressure, and then toluene was added. The mixture was heated to remove as much water and acetic acid as possible in the form of azeotropes. The residue was purified by column chromatography through silica gel eluted with a 1:1 by volume mixture of chloroform and ethyl acetate, giving 0.56 g of the title compound in the form of a powder.

Infrared Absorption Spectrum (Nujol mull)
$v_{max}$ cm$^{-1}$:3430, 1735.

Nuclear Magnetic Resonance Spectrum (CDCl$_3$) δ ppm:
1.53 (3H, singlet, 14—CH$_3$);
1.82 (3H, broad singlet, 4—CH$_3$);
2.67-3.22 (3H, multiplet, 2×OH & 25—H);
3.43-3.85 (3H, multiplet, —CH$_2$OH & 17—H);
3.86-4.13 (1H, multiplet, 2—H̄ of propyl);
4.12 (1H, doublet, J=6.5Hz, 6—H);
4.24 (1H, singlet, 7—OH);
4.13-4.45 (2H, multiplet, 1—H of propyl×2);
4.66 (2H, broad singlet, 26—CH$_2$).

Mass Spectrum (m/e): 556, 429, 410.

EXAMPLE 10

$O^5$-(2,2-Dimethyl-1,3-dioxolan-4-ylmethoxycarbonyl)milbemycin A$_4$

The procedure described in Example 8 was repeated, but using 0.50 g of milbemycin A$_4$, 0.5 ml of pyridine and 1.30 g of 2,2-dimethyl-1,3-dioxlan-4-ylmethyl chloroformate, to give 0.589 g of the title compound in a vitreous state.

Nuclear Magnetic Resonance Spectrum (CDCl$_3$) δ ppm:
1.36 (3H, singlet, 2-methyl of dioxolane);
1.44 (3H, singlet, 2-methyl of dioxolane);
1.53 (3H, singlet, 14—CH$_3$);
1.81 (3H, singlet, 4—CH$_3$);
3.80 (1H, singlet, 7—OH);
4.64 (2H, broad singlet, 26-methylene).

Mass Spectrum (m/e): 699, 523, 506.

EXAMPLE 11

$O^5$-(2,3-Dihydroxypropoxycarbonyl-milbemycin A$_4$

The procedure described in Example 9 was repeated, but using 593 mg of $O^5$-(2,2-dimethyl-1,3-dioxolan-4-ylmethoxycarbonyl)milbemycin A$_4$ (prepared as described in Example 10 above), to give 335 mg of the title compound in the form of a powder.

Infrared Absorption Spectrum (Nujol mull)
$v_{max}$ cm$^{-1}$:3460, 1745.

Nuclear Magnetic Resonance Spectrum (CDCl$_3$) δ ppm:
1.53 (3H, singlet, 14—CH$_3$);
1.82 (3H, singlet, 4—CH$_3$);
3.08 (1H, triplet, 25—H);
3.33 (1H, multiplet, 2—H);
3.6-3.75 (2H, multiplet, CH(OH)CH$_2$OH);
3.99 (1H, multiplet, CH(OH)CH$_2$ŌH);
4.12 (1H, doublet, 6—H̄);
4.2-4.35 (2H, multiplet, OCH$_2$CH(OH)CH$_2$OH);
4.64 (2H, broad singlet, 26-methylene).

Mass Spectrum (m/e):542, 414, 396.

EXAMPLE 12

Anthelmintic activity against larvae of *Ascaris suum* migrating into the lungs of mice The test animals employed were male mice of the ddy strain each weighing 25-30 g. The animals were employed in groups of 5 for each test. At the beginning of the experiment, each mouse (except those in a control, non-infected group) were infected with *Ascaris suum* by orally administering about 3,000 eggs per mouse through a stomach tube.

24 hours after infection, the compound under test was administered (except to the control, non-infected group and a control, infected group) either orally or by subcutaneous injection at a dose of 0.8 mg/kg body weight per mouse. The test compound was administrated as a formulation prepared by mixing 1.0 g of the test compound, 0.1 g of butylated hydroxytoluene and 10 ml of acetamide with sufficient polyethylene glycol (PEG-400) to give a total volume of 100 ml.

On the 7th day after infection, the mice were killed and autopsied to determine the extent of lesions in the lungs and the number of larvae that had migrated into the lungs. The extent of the lesions was rated according to the method of Brown et al. [Am. J. Vet. Res. 16, 613–615 (1955)]. The larvae were collected by Berman's method and then the number of larvae was calculated by the dilution method.

The body weight of each mouse was measured just prior to infection and on autopsy. The maintenance of the body weight was calculated as the change in body weight between the two measurements divided by the average change in body weight of the mice of the control, non-infected group, and expressed as a percentage.

The decrease in the number of larvae was calculated as the difference between the average number of larvae in the control, infected group and the number of larvae in the group under test divided by the number of larvae in the control, infected group and expressed as a percentage.

The results are shown in Tables 1 (for oral administration) and 2 (for subcutaneous injection).

TABLE 1

| | (oral administration) | | |
|---|---|---|---|
| | Extent of lesions | Maintenance of body weight (%) | Decrease in larvae (%) |
| Compound of Ex. No. | | | |
| 1(a) | 3.6 | 80.2 | 65.1 |
| 4 | 3.4 | 79.8 | 66.9 |
| 6 | 3.4 | 80.5 | 65.5 |
| 7 | 3.4 | 86.1 | 70.8 |
| 9 | 3.0 | 83.0 | 65.3 |
| Controls: | | | |
| Non-infected | 0 | 100 | — |
| Infected | 3.5 | 81.1 | 0 |

TABLE 2

| | (subcutaneous administration) | | |
|---|---|---|---|
| | Extent of lesions | Maintenance of body weight (%) | Decrease in larvae (%) |
| Compound of Ex. No. | | | |
| 1(a) | 3.6 | 81.4 | 67.9 |
| 4 | 3.4 | 81.9 | 61.1 |
| 6 | 3.6 | 81.3 | 65.5 |
| 7 | 3.4 | 84.4 | 69.6 |
| 9 | 3.4 | 78.8 | 58.3 |
| Controls: | | | |
| Non-infected | 0 | 100 | — |
| Infected | 4.0 | 81.2 | 0 |

EXAMPLE 13

Anthelmintic activity against *Derofilaria immitis*

Dogs having a body weight of 8 to 17 kg, naturally infected by *Derofilaria immitis*, were used as the test animals.

1.0 g of each of the test compounds listed in Tables 3 and 4 was blended with 0.1 g of butylated hydroxytoluene, 10 ml of acetamide and sufficient polyethylene glycol (PEG-400) to bring the total volume to 100 ml.

Each dog was then given orally or by subcutaneous injection sufficient of this composition to provide 0.1 mg of the test compound per kilogram body weight.

A sample of blood was drawn from the dog's saphena immediately prior to administration of the composition and then one week and two weeks after administration. Using a Zahli pipette, 0.02 ml of the blood sample was smeared thickly onto a glass slide, and then the blood was stained with Giemsa solution and the number of microfilaria was counted microscopically and determined as an average over four glass slides.

The results are reported in Tables 3 and 4 as the percentage reduction of microfilaria from the value before administration of the composition to that achieved 1 or 2 weeks after administration.

TABLE 3

| | (Oral Administration) | |
|---|---|---|
| Compound of Ex. | % Reduction of Microfilaria | |
| | After 1 week | After 2 weeks |
| 1(a) | 80.1 | 83.3 |
| 3 | 83.8 | 85.1 |
| 6 | 95.5 | 94.9 |
| 9 | 99.4 | 99.6 |
| 10 | 84.3 | 54.5 |

TABLE 4

| | (Subcutaneous Injection) | |
|---|---|---|
| Compd. of Ex. | % Reduction of Microfilaria | |
| | After 1 week | After 2 weeks |
| 1(a) | 42.8 | 79.8 |
| 3 | 72.6 | 74.1 |
| 6 | 97.7 | 97.6 |
| 9 | 88.9 | 88.0 |

EXAMPLE 14

Acaricidal activity against *Tetranychus urticae*

The primary leaves of plants of the species *Phaseolus vulgaris* were infected by contact with a piece of leaf from a mass culture of acarids of the species *Tetranychus urticae* (organic phosphate-sensitive). 16 hours after infection, the infested plants were sprayed, until dripping wet, with a test solution containing the compound under test at a concentration of 0.2, 0.6 or 1.0 ppm. The plants were assessed after 24 hours and again after 7 days by examining imagos and larvae (all mobile stages) under a binocular microscope, to determine living and dead individuals. One plant was used for each concentration and each test compound. The plants were kept during the test in greenhouse compartments at 25° C. Each of the compounds of Examples 1 to 11 achieved 100% mortality within the test period against acarids of the species *Tetranychus urticae* at concentrations within the range from 0.6 to 1.0 ppm.

We claim:

1. A compound of formula (II):

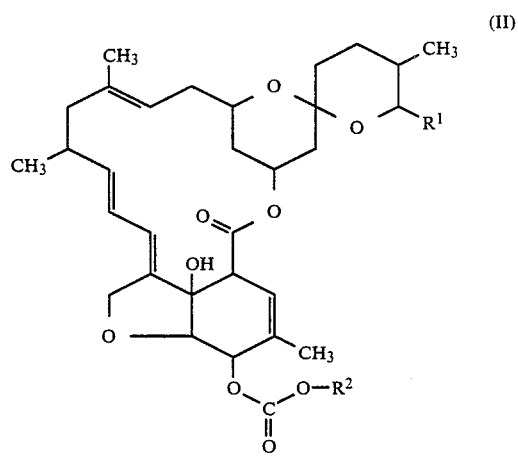

(II)

wherein $R^1$ is selected from the group consisting of methyl, ethyl and isopropyl groups;

$R^2$ is selected from the group consisting of (i) a group formed from a protected or unprotected sugar alcohol, sugar or aldonic acid by removal of the ω-alcoholic hydroxy group therefrom, and wherein the sugar alcohol is glycerol, erythritol, threitol, arabitol, adonitol, xylitol, sorbitol, mannitol or dulcitol and the sugar is glyceraldehyde, an aldose, a ketose, or a disaccharide and (ii) a group of the formula —A—$R^3$;

A is selected from the group consisting of $C_1$-$C_6$ alkylene and $C_1$-$C_6$ alkylidene groups;

$R^3$ is selected from the group consisting of a hydrogen atom, a halogen atom, a group of formula —Q—$R^4$, a group of formula —O.CO.$R^5$ and a group of formula —NH.CO.$R^6$;

Q is selected from the group consisting of an oxygen atom, a sulfur atom and the imino group;

$R^4$ is selected from the group consisting of hydrogen, a $C_1$-$C_6$ alkyl alkyl group and a substituted $C_1$-$C_6$ alkyl group;

$R^5$ is selected from the group consisting of a $C_1$-$C_6$ alkyl group, a substituted $C_1$-$C_6$ alkyl group, phenyl, tolyl, naphthyl, a 5- or 6- membered heterocyclic group containing a ring oxygen or a ring sulfur and a group formed from an unprotected or a protected aldonic or uronic acid by removal of one carboxy group;

$R^6$ is selected from the group consisting of a $C_1$-$C_6$ alkyl group, phenyl, tolyl and naphthyl; and the substituents on said substituted $C_1$-$C_6$ alkyl groups are at least one group selected from the group consisting of hydroxy, $C_1$-$C_6$ alkoxy, aryloxy, amino, acylamino, $C_1$-$C_6$ alkylamino, di($C_1$-$C_6$ alkyl) amino, arylamino, mercapto, $C_1$-$C_6$ alkylthio and arylthio groups and wherein the aryl moieties are selected from the group consisting of phenyl, tolyl or naphthyl.

2. The compound of claim 1, in which $R^2$ is said group formed from said unprotected or protected sugar alcohol by removing the ω-alcoholic hydroxy group.

3. The compound of claim 1, in which $R^2$ represents a group of formula —A—$R^3$ wherein:

A represents a $C_1$-$C_2$ alkylene group;

$R^3$ represents a halogen atom, a group of formula —Q—$R^4$ or a group of formula —OCO$R^5$;

Q represents an oxygen or sulfur atom;

$R^4$ represents a $C_1$-$C_3$ alkyl group or a substituted $C_1$-$C_3$ alkyl group, the substituent being selected from the group consisting of the hydroxy group, $C_1$-$C_3$ alkoxy groups, the amino group, acetylamino groups and mono- and di-($C_1$-$C_3$ alkyl)amino groups; and $R^5$ represents a $C_1$-$C_3$ alkyl groups, a substituted $C_1$-$C_3$ alkyl group, the substituent being the same as defined for $R^4$ above, a 5- or 6-membered heterocyclic group containing the oxygen atom or a group formed from an unprotected or protected aldonic acid by removing the carboxy group.

4. The compound of claim 1 or claim 2, in which $R^1$ represents an ethyl or isopropyl group.

5. The compound of claim 1 designated $O^5$-(Chloromethoxycarbonyl)milbemycin D

6. The compound of claim 1 designated $O^5$-(3,4-Dihydro-2H-pyran-2-ylcarbonyloxy)methoxycarbonylmilbemycin D 7. The compound of claim 1 designated $O^5$-(1,2,3,4-Di-O-isopropylidenegalacturonyloxy)methoxycarbonylmilbemycin D 8. The compound of claim 1 designated $O^5$-(4-Hydroxybutyryloxymethoxycarbonyl)milbemycin D 9. The compound of claim 1 designated $O^5$-[2-(N,N-Dimethylamino)ethylthiomethoxycarbonyl]milbemycin D 10. The compound of claim 1 designated $O^5$-(2,3-Dihydroxypropoxycarbonyl)milbemycin $A_4$.

11. The compound of claim 1 designated $O^5$-(2,3-Dihydroxypropoxycarbonyl)milbemycin D.

12. The compound of claim 1 designated $O^5$-(2,2-Dimethyl-1,3-dioxolan-4-ylmethoxycarbonyl)milbemycin $A_4$.

13. An antihelmintic composition comprising 0.0001 to 50% by weight of an anthelmintic, compound in admixture with a pharmaceutically acceptable carrier or diluent, wherein the compound is selected from the group consisting of compounds of formula (II):

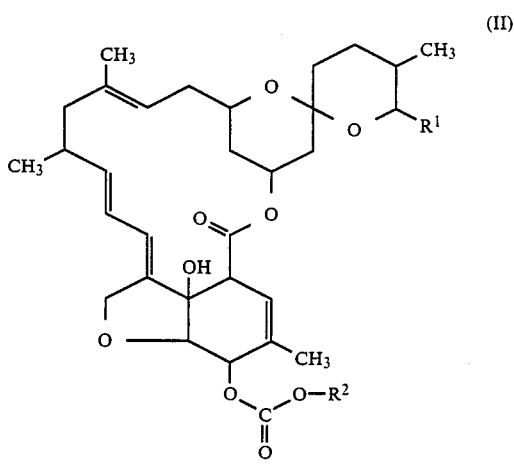

(II)

wherein $R^1$ is selected from the group consisting of methyl, ethyl and isopropyl groups;

$R^2$ is selected from the group consisting of (i) a group formed from a protected or unprotected sugar alcohol, sugar or aldonic acid by removal of the ω-alcoholic hydroxy group therefrom, and wherein the sugar alcohol is glycerol, erythritol, threitol, arabitol, adonitol, xylitol, sorbitol, mannitol or dulcitol and the sugar is glyceraldehyde, an aldose, a ketose, or a disaccharide and (ii) a group of the formula —A—$R^3$;

A is selected from the group consisting of $C_1$-$C_6$ alkylene and $C_1$-$C_6$ alkylidene groups;

$R^3$ is selected from the group consisting of a hydrogen atom, a halogen atom, a group of formula —Q—$R^4$ , a group of formula —O.CO.$R^5$ and a group of formula —NH.CO.$R^6$;

Q is selected from the group consisting of an oxygen atom, a sulfur atom and the imino group;

$R^4$ is selected from the group consisting of hydrogen, a $C_1$-$C_6$ alkyl group and a substituted $C_1$-$C_6$ alkyl group;

$R^5$ is selected from the group consisting of a $C_1$-$C_6$ alkyl group, a substituted $C_1$-$C_6$ alkyl group, phenyl, tolyl, naphthyl, a 5- or 6- membered heterocyclic group containing a ring oxygen or a ring sulfur and a group formed from an unprotected or 2 protected aldonic or uronic acid by removal of one carboxy group;

$R^6$ is selected from the group consisting of a $C_1$-$C_6$ alkyl group phenyl, tolyl and naphthyl; and the substituents on said substituted $C_1$-$C_6$ alkyl groups are at least one group selected from the group consisting of hydroxy, $C_1$–$C_6$ alkoxy, aryloxy, amino, acylamino, $C_1$–$C_6$ alkylamino, di($C_1$–$C_6$alkyl) amino, arylamino, mercapto, $C_1$–$C_6$ alkylthio and arylthio groups and wherein the aryl moieties are selected from the group consisting of phenyl, tolyl or naphthyl.

14. The composition of claim 13, in which $R^2$ is said group formed from the unprotected or protected sugar alcohol by removing the ω-alcoholic hydroxy group.

15. The composition of claim 13, in which $R^2$ represents a group of formula —A—$R^3$ wherein:

A represents a $C_1$–$C_2$ alkylene group;

$R^3$ represents a halogen atom, a group of formula —Q—$R^4$ or a group of formula —OCO$R^5$;

Q represents an oxygen or sulfur atom;

$R^4$ represents a $C_1$–$C_3$ alkyl group or a substituted $C_1$–$C_3$ alkyl group, the substituent being selected from the group consisting of the hydroxy group, $C_1$–$C_3$ alkoxy groups, the amino group, acetylamino groups and mono- and di-($C_1$–$C_3$ alkyl)amino groups; and $R^5$ represents a $C_1$–$C_3$ alkyl group, a substituted $C_1$–$C_3$ alkyl group, the substituent being the same as defined for $R^4$ above, a 5- or 6-membered heterocyclic group containing the oxygen atom or a group formed from an unprotected or protected aldonic acid by removing the carboxy group.

16. The composition claim 13 or claim 14, in which $R^1$ represents an ethyl or isopropyl group.

17. The composition of claim 13, in which said compound is selected from the group consisting of:

$O^5$-(Chloromethoxycarbonyl)milbemycin D $O^5$-(3,4-Dihydro-2H-pyran-2-ylcarbonyloxy)methoxycarbonylmilbemycin D $O^5$-(1,2,3,4-Di-O-isopropylidenegalacturonyloxy)methoxycarbonylmilbemycin D $O^5$-(4-Hydroxybutyryloxymethoxycarbonyl)milbemycin D $O^5$-[2-(N,N-Dimethylamino)ethylthiomethoxycarbonyl]milbemycin D $O^5$-(2,3-Dihydroxypropoxycarbonyl)milbemycin $A_4$ $O^5$-(2,3-Dihydroxypropoxycarbonyl)milbemycin D and $O^5$-(2,2-Dimethyl-1,3-dioxolan-4-ylmethoxycarbonyl)milbemycin $A_4$.

18. An acaricidal or insecticidal composition comprising 0.01–99% by weight of the compound of claim 1 in an agriculturally or horticulturally acceptable carrier or diluent.

19. A method of protecting a plant from damage by parasites selected from the group consisting of acarids, helminths and insects, which comprises applying an effective amount of the compound of claim 1 to the plants, their seeds or the locus including same, to combat parasite damage.

20. A method of treating an animal parasitized by a parasite selected from helminths, acarids and insects, which comprises applying to or administering to said animal an effective amount of active compound, wherein said active compound is selected from the group consisting of compounds of formula (II):

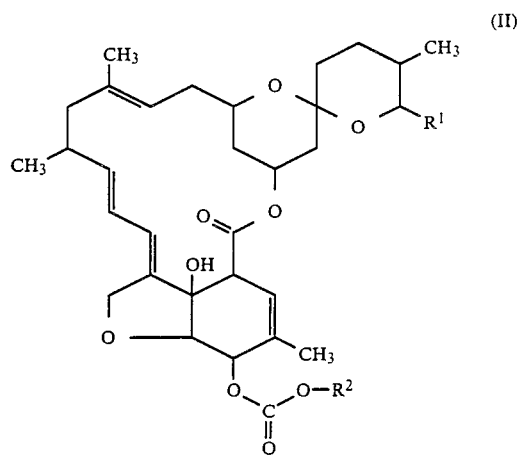

wherein $R^1$ is selected from the group consisting of methyl, ethyl and isopropyl groups;

$R^2$ is selected from the group consisting of (i) a group formed from a protected or unprotected sugar alcohol, sugar or aldonic acid by removal of the ω-alcoholic hydroxy group therefrom, and wherein the sugar alcohol is glycerol, erythritol, threitol, arabitol, adonitol, xylitol, sorbitol, mannitol or dulcitol and the sugar is glyceraldehyde, an aldose, a ketose, or a disaccharide and (ii) a group of the formula —A—$R^3$;

A is selected from the group consisting of $C_1$–$C_6$ alkylene and $C_1$–$C_6$ alkylidene groups;

$R^3$ is selected from the group consisting of a hydrogen atom, a halogen atom, a group of formula —Q—$R^4$, a group of formula —O.CO.$R^5$ and a group of formula —NH.CO.$R^6$;

Q is selected from the group consisting of an oxygen atom, a sulfur atom and the imino group;

$R^4$ is selected from the group consisting of hydrogen, a $C_1$–$C_6$ alkyl group and a substituted $C_1$–$C_6$ alkyl group;

$R^5$ is selected from the group consisting of a $C_1$–$C_6$ alkyl group, a substituted $C_1$–$C_6$ alkyl group, phenyl, tolyl, naphthyl, a 5- or 6- membered cyclic heterocyclic group containing a ring oxygen or a ring sulfur and a group formed from an unprotected or a protected aldonic or uronic acid by removal of one carboxy group;

$R^6$ is selected from the group consisting of a $C_1$–$C_6$ alkyl group, phenyl, tolyl and naphthyl; and the substituents on said substituted $C_1$–$C_6$ alkyl groups are at least one group selected from the group consisting of hydroxy, $C_1$–$C_6$ alkoxy, aryloxy, amino, acylamino, $C_1$–$C_6$ alkylamino, di($C_1$–$C_6$ alkyl)amino, arylamino, mercapto, $C_1$–$C_6$ alkylthio and arylthio groups and wherein the aryl moieties are selected from the group consisting of pheynyl, tolyl or naphthyl.

21. A method as claimed in claim 20, in which $R^2$ represents a group formed from an unprotected or a protected sugar alcohol by removing the ω-alcoholic hydroxy group.

22. The method of claim 20, in which $R^2$ represents a group of formula —A—$R^3$ wherein:

A represents a $C_1$–$C_2$ alkylene group;

R[3] represents a halogen atom, a group of formula —Q—R[4] or a group of formula —OCOR[5];

Q represents an oxygen or sulfur atom;

R[4] represents a $C_1$-$C_3$ alkyl group or a substituted $C_1$-$C_3$ alkyl group, the substituent being selected from the group consisting of the hydroxy group, $C_1$-$C_3$ alkoxy groups, the amino group, acetylamino groups and mono- and di-($C_1$-$C_3$ alkyl)amino groups; and R[5] represents a $C_1$-$C_3$ alkyl group, a substituted $C_1$-$C_3$ alkyl group, the substituent being the same as defined for R[4] above, a 5- or 6-membered heterocyclic group containing the oxygen atom or a group formed from an unprotected or protected aldonic acid by removing the carboxy group.

23. The method of claim 20 or claim 21, in which R[1] represents an ethyl or isopropyl group.

24. The method as claimed in claim 20, 18 or 19 in which said compound is selected from the group consisting of:
 O[5]-(Chloromethoxycarbonyl)milbemycin D
 O[5]-(3,4-Dihydro-2H-pyran-2-ylcarbonyloxy)methoxycarbonylmilbemycin D
 O[5]-(1,2,3,4-Di-O-isopropylidenegalacturonyloxy)methoxycarbonylmilbemycin D
 O[5]-(4-Hydroxybutyryloxymethoxycarbonyl)milbemycin D
 O[5]-[2-(N,N-Dimethylamino)ethylthiomethoxycarbonyl]milbemycin D
 O[5]-(2,3-Dihydroxypropoxycarbonyl)milbemycin $A_4$
 O[5]-(2,3-Dihydroxypropoxycarbonyl)milbemycin D and
 O[5]-(2,2-dimethyl-1,3-dioxolan-4-ylmethoxycarbonyl)milbemycin $A_4$.

25. A method of protecting an animal from damage by parasites selected from the group consisting of acarids, helminths and insects, which comprises applying an effective amount of active compound to said animal wherein the active compound is selected from the group consisting of compounds of formula (II):

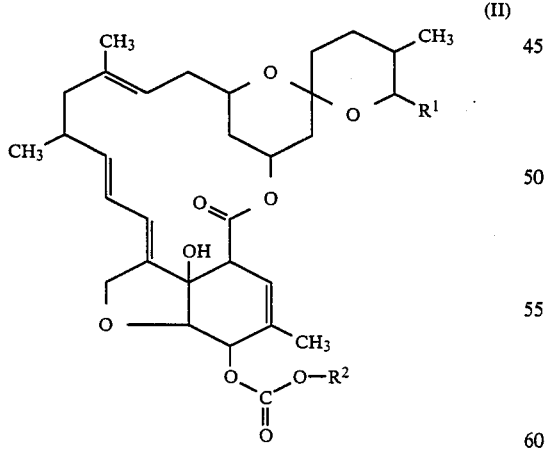

(II)

wherein
 R[1] is selected from the group consisting of methyl, ethyl and isopropyl groups;
 R[2] is selected from the group consisting of (i) a group formed from an optionally protected sugar alcohol, sugar or aldonic acid by removal of the ω-alcoholic hydroxy group therefrom, and (ii) a group of the formula —A—R[3];
 A is selected from the group consisting of alkylene and alkylidene groups;
 R[3] is selected from the group consisting of a hydrogen atom, a halogen atom, a group of formula —Q—R[4], a group of formula —O.CO.R[5] and a group of formula —NH.CO.R[6];
 Q is selected from the group consisting of an oxygen atom, a sulfur atom and the imino group;
 R[4] is selected from the group consisting of hydrogen, a $C_1$-$C_6$ alkyl group and a substituted $C_1$-$C_6$ alkyl group;
 R[5] is selected from the group consisting of a $C_1$-$C_6$ alkyl group, a substituted $C_1$-$C_6$ alkyl group, an aryl group, a heterocyclic group and a group formed from an optionally protected aldonic or uronic acid by removal of one carboxy group;
 R[6] is selected from the group consisting of a $C_1$-$C_6$ alkyl group and an aryl group; and
 the substituents on said substituted $C_1$-$C_6$ alkyl groups are at least one group selected from the group consisting of hydroxy, $C_1$-$C_6$ alkoxy, aryloxy, amino, acylamino, $C_1$-$C_6$ alkylamino, di($C_1$-$C_6$ alkyl)amino, arylamino, mercapto, $C_1$-$C_6$ alkylthio and arylthio groups.

26. A method as claimed in claim 25, in which R[2] represents a group formed from an unprotected or a protected sugar alcohol by removing the ω-alcoholic hydroxy group.

27. The method of claim 25, in which R[2] represents a group of formula —A—R[3] wherein:
 A represents a $C_1$-$C_2$ alkylene group;
 R[3] represents a halogen atom, a group of formula —Q—R[4] or a group of formula —OCOR[5];
 Q represents an oxygen or sulfur atom;
 R[4] represents a $C_1$-$C_3$ alkyl group or a substituted $C_1$-$C_3$ alkyl group, the substituent being selected from the group consisting of the hydroxy group, $C_1$-$C_3$ alkoxy groups, the amino group, acetylamino groups and mono- and di-($C_1$-$C_3$ alkyl)amino groups; and
 R[5] represents a $C_1$-$C_3$ alkyl group, a substituted $C_1$-$C_3$ alkyl group, the substituent being the same as defined for R[4] above, a 5- or 6-membered heterocyclic group containing the oxygen atom or a group formed from an unprotected or protected aldonic acid by removing the carboxy group.

28. The method of claim 25 or claim 26, in which R[1] represents an ethyl or isopropyl group.

29. The method of claim 25, in which said compound is selected from the group consisting of:
 O[5]-(Chloromethoxycarbonyl)milbemycin D
 O[5]-(3,4-Dihydro-2H-pyran-2-ylcarbonyloxy)methoxycarbonylmilbemycin D
 O[5]-(1,2,3,4-Di-O-isopropylidenegalacturonyloxy)methoxycarbonylmilbemycin D
 O[5]-(4-Hydroxybutyryloxymethoxycarbonyl)milbemycin D
 O[5]-[2-(N,N-Dimethylamino)ethylthiomethoxycarbonyl]milbemycin D
 O[5]-(2,3-Dihydroxypropoxycarbonyl)milbemycin $A_4$
 O[5]-(2,3-Dihydroxypropoxycarbonyl)milbemycin D and
 O[5]-(2,2-Dimethyl-1,3-dioxolan-4-ylmethoxycarbonyl)milbemycin $A_4$.

* * * * *

UNITED STATES PATENT AND TRADEMARK OFFICE
CERTIFICATE OF CORRECTION

PATENT NO. : 4,760,054
DATED : July 26, 1988
INVENTOR(S) : IDE et al It is certified that error appears in the above-identified patent and that said Letters Patent is hereby corrected as shown below:

Column 21, line 16 (Claim 1):
    before "group" delete "alkyl".

Column 22, line 64 (Claim 13):
    before "protected" delete "2" and
    insert -- a --.

Column 25, line 19 (Claim 24):
    after "claim 20," delete "18 or 19". And insert --Claim 18 or Claim 19--.

Signed and Sealed this

Eighteenth Day of May, 1993

Attest:

MICHAEL K. KIRK

*Attesting Officer*      *Acting Commissioner of Patents and Trademarks*